United States Patent
Sevensma

(10) Patent No.: US 9,636,480 B2
(45) Date of Patent: May 2, 2017

(54) STEERABLE CATHETERS

(71) Applicant: Matthew W. Sevensma, Grand Rapids, MI (US)

(72) Inventor: Matthew W. Sevensma, Grand Rapids, MI (US)

(*) Notice: Subject to any disclaimer, the term of this patent is extended or adjusted under 35 U.S.C. 154(b) by 800 days.

(21) Appl. No.: 13/801,888

(22) Filed: Mar. 13, 2013

(65) Prior Publication Data

US 2014/0276612 A1  Sep. 18, 2014

(51) Int. Cl.
  *A61M 25/01*  (2006.01)
  *A61M 25/00*  (2006.01)

(52) U.S. Cl.
  CPC ..... *A61M 25/0136* (2013.01); *A61M 25/0041* (2013.01); *A61M 25/0147* (2013.01); *A61M 2025/0175* (2013.01)

(58) Field of Classification Search
  CPC ...... A61M 25/0074; A61M 2025/0079; A61M 25/008; A61M 25/01; A61M 25/0105; A61M 25/0133; A61M 25/0136; A61M 25/0147; A61M 2025/015; A61M 2025/0186
  See application file for complete search history.

(56) References Cited

U.S. PATENT DOCUMENTS

| | | | | |
|---|---|---|---|---|
| 4,760,848 A | * | 8/1988 | Hasson | A61B 17/062 294/115 |
| 4,986,257 A | * | 1/1991 | Chikama | A61B 1/0052 600/146 |
| 5,282,817 A | * | 2/1994 | Hoogeboom | A61B 17/2909 606/167 |
| 5,318,525 A | | 6/1994 | West et al. | |
| 5,355,871 A | * | 10/1994 | Hurley | A61B 17/00234 604/159 |
| 5,397,304 A | | 3/1995 | Truckai | |
| 5,549,627 A | * | 8/1996 | Kieturakis | A61B 17/29 606/206 |
| 5,741,270 A | * | 4/1998 | Hansen | A61B 17/2909 606/108 |
| 5,779,699 A | | 7/1998 | Lipson | |
| 5,989,241 A | * | 11/1999 | Plishka | A61M 25/0147 604/540 |
| 7,717,875 B2 | | 5/2010 | Knudson et al. | |
| 7,780,648 B2 | | 8/2010 | McIntyre et al. | |

(Continued)

*Primary Examiner* — Imani Hayman
*Assistant Examiner* — Laura Schell
(74) *Attorney, Agent, or Firm* — Knobbe, Martens, Olson & Bear, LLP

(57) ABSTRACT

Embodiments of steerable catheters are disclosed. The catheters may include a plurality of generally arcuate-shaped struts connected at proximal and distal ends of a handle. The handle is connected to a tubular portion at a distal end of the handle. The tubular portion includes a resilient component positioned near a distal tip of the tubular portion. The catheter includes a pull wire fixed to a point at or near the distal tip of the tubular portion. Upon manual compression of the handle, the struts are squeezed together, lengthening the handle, and extending the pull wire proximally. The proximal extension of the pull wire can cause the distal tip of the catheter to deflect. The catheter can be rotated greater than 360° around a longitudinal axis. The compressible handle can allow a user of the catheter tactile feedback and control over navigation of the catheter.

16 Claims, 8 Drawing Sheets

(56) References Cited

U.S. PATENT DOCUMENTS

| | | | |
|---|---|---|---|
| 7,955,314 B2 | 6/2011 | Fischer et al. | |
| 2006/0258979 A1* | 11/2006 | Fischer | A61M 25/0136 604/95.04 |
| 2007/0135733 A1* | 6/2007 | Soukup | A61M 25/0136 600/585 |
| 2010/0095969 A1* | 4/2010 | Schwartz | A61M 25/0136 128/207.14 |
| 2011/0245828 A1 | 10/2011 | Baxter et al. | |
| 2011/0301536 A1 | 12/2011 | Rashidi | |
| 2013/0060240 A1* | 3/2013 | Scheller | A61B 18/22 606/4 |

* cited by examiner

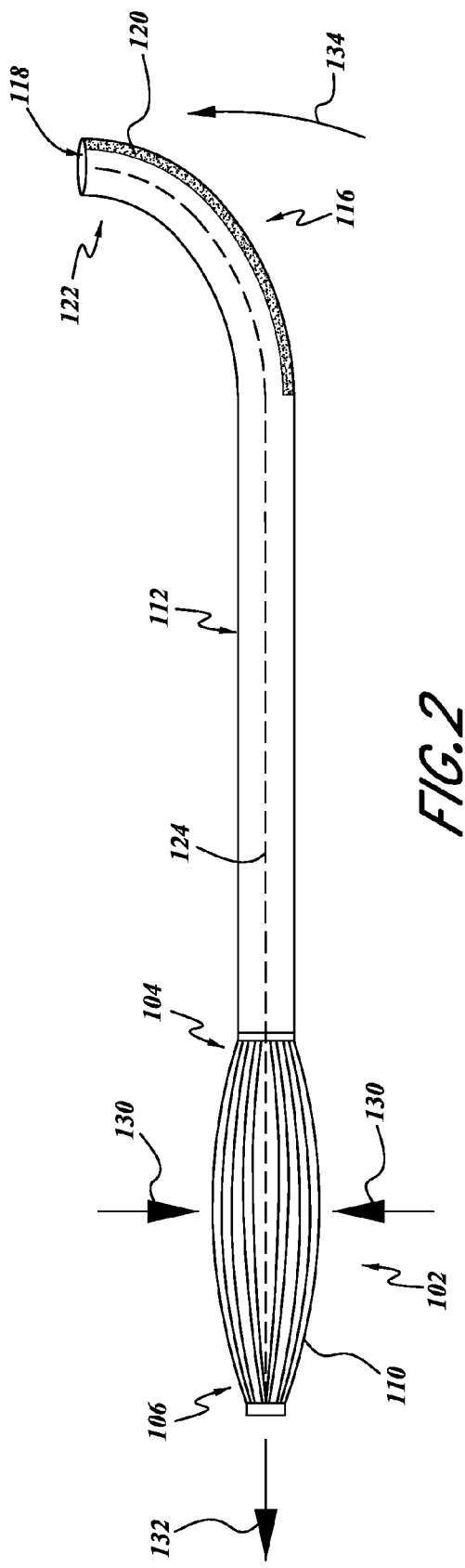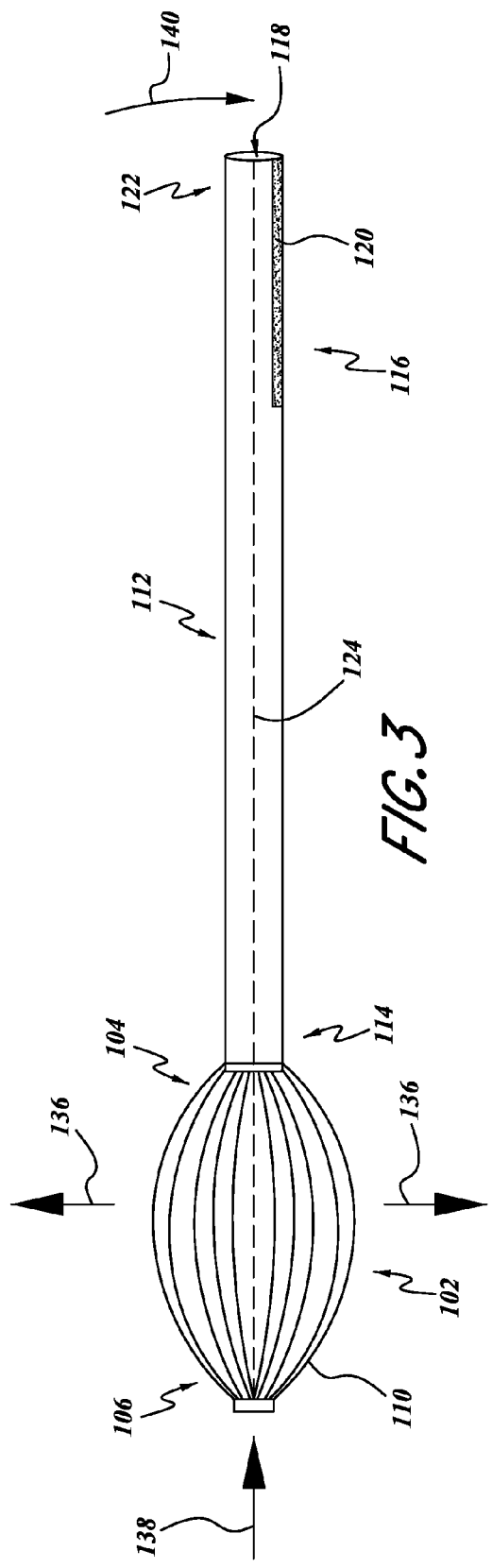

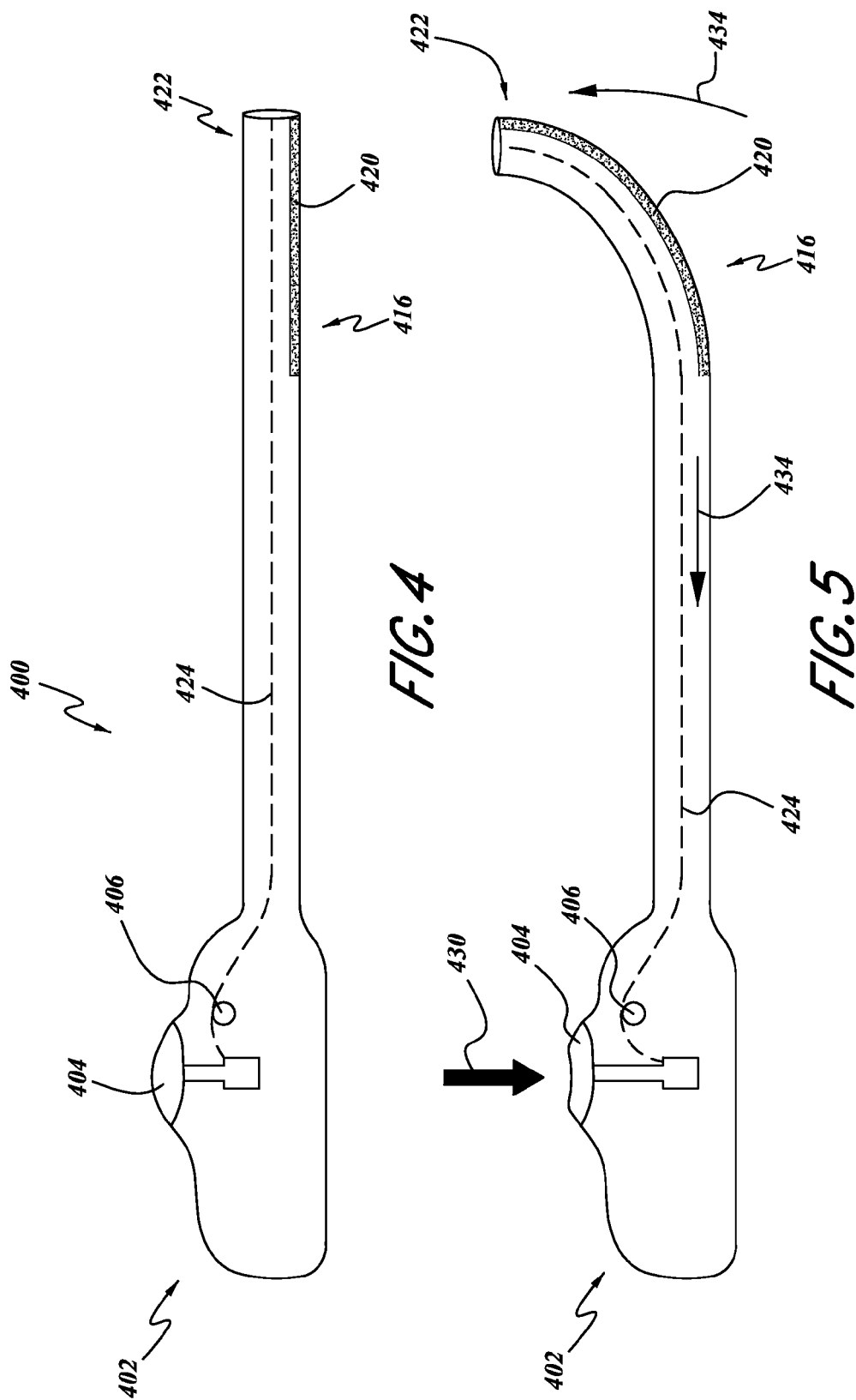

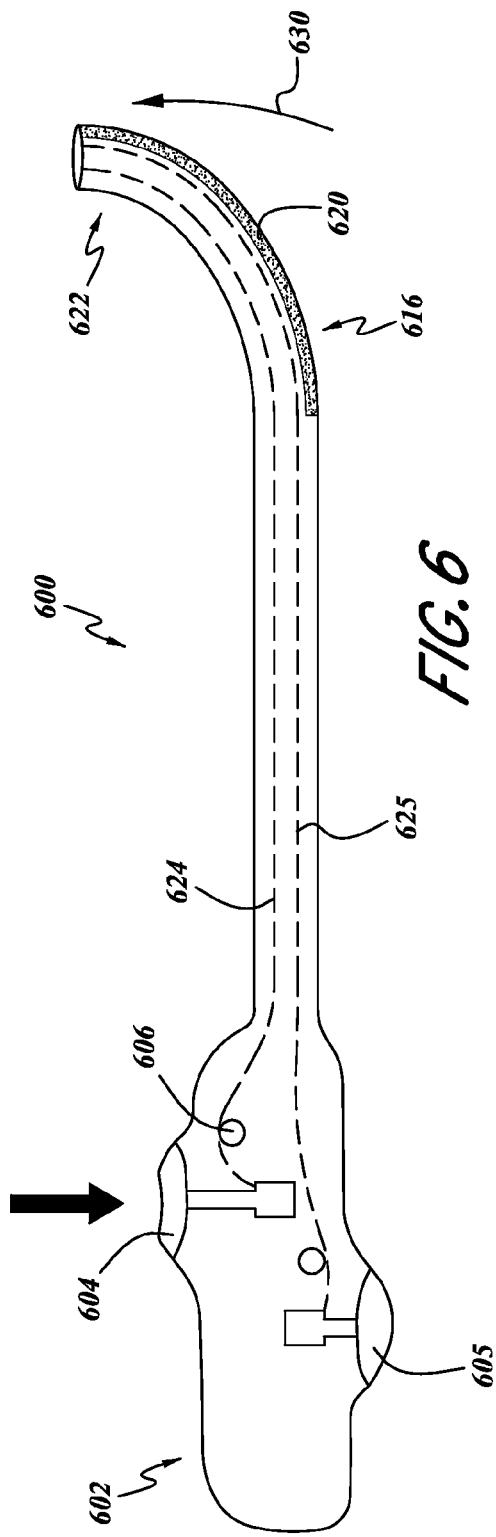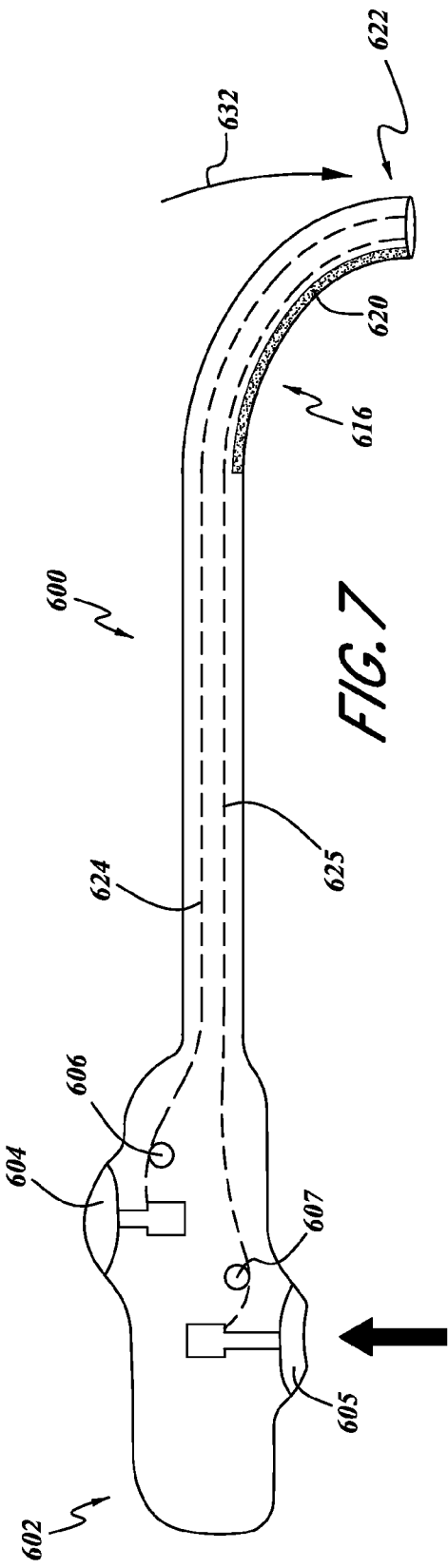

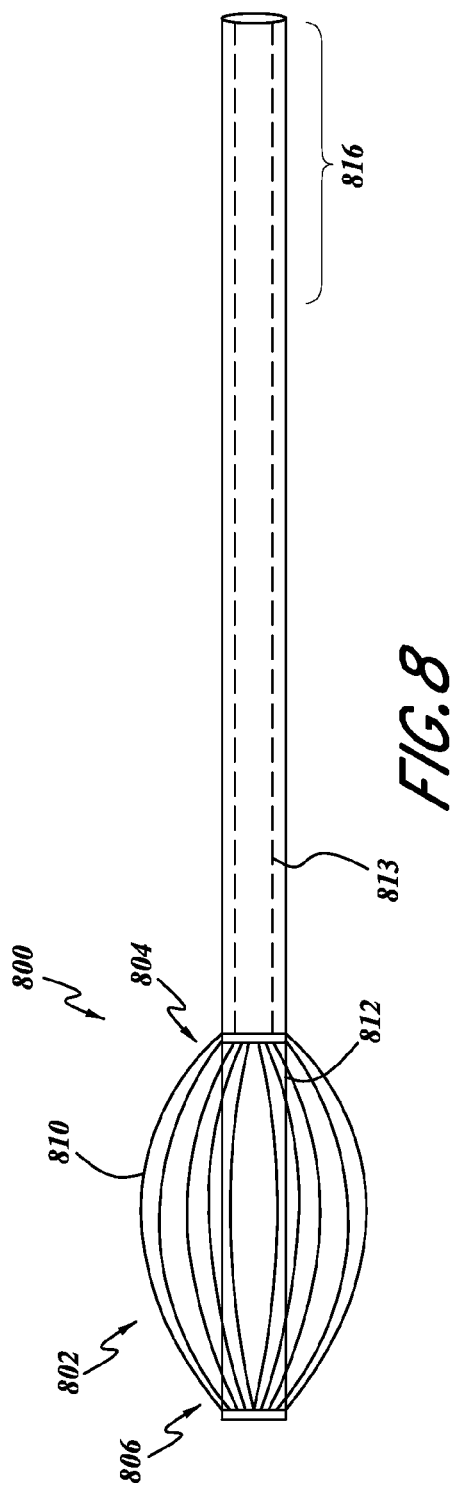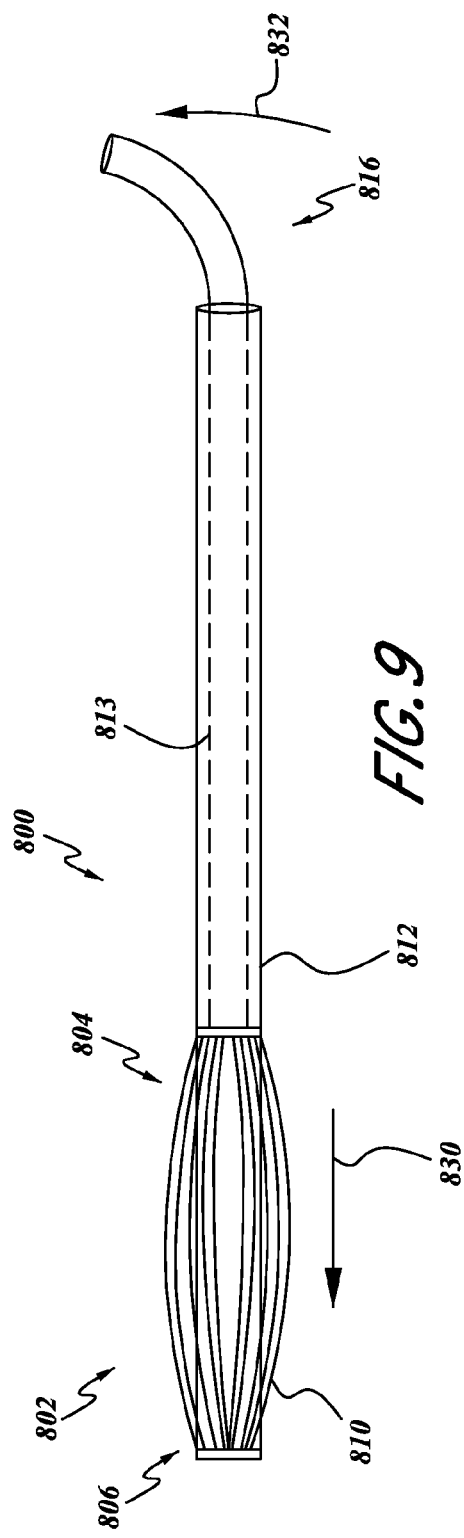

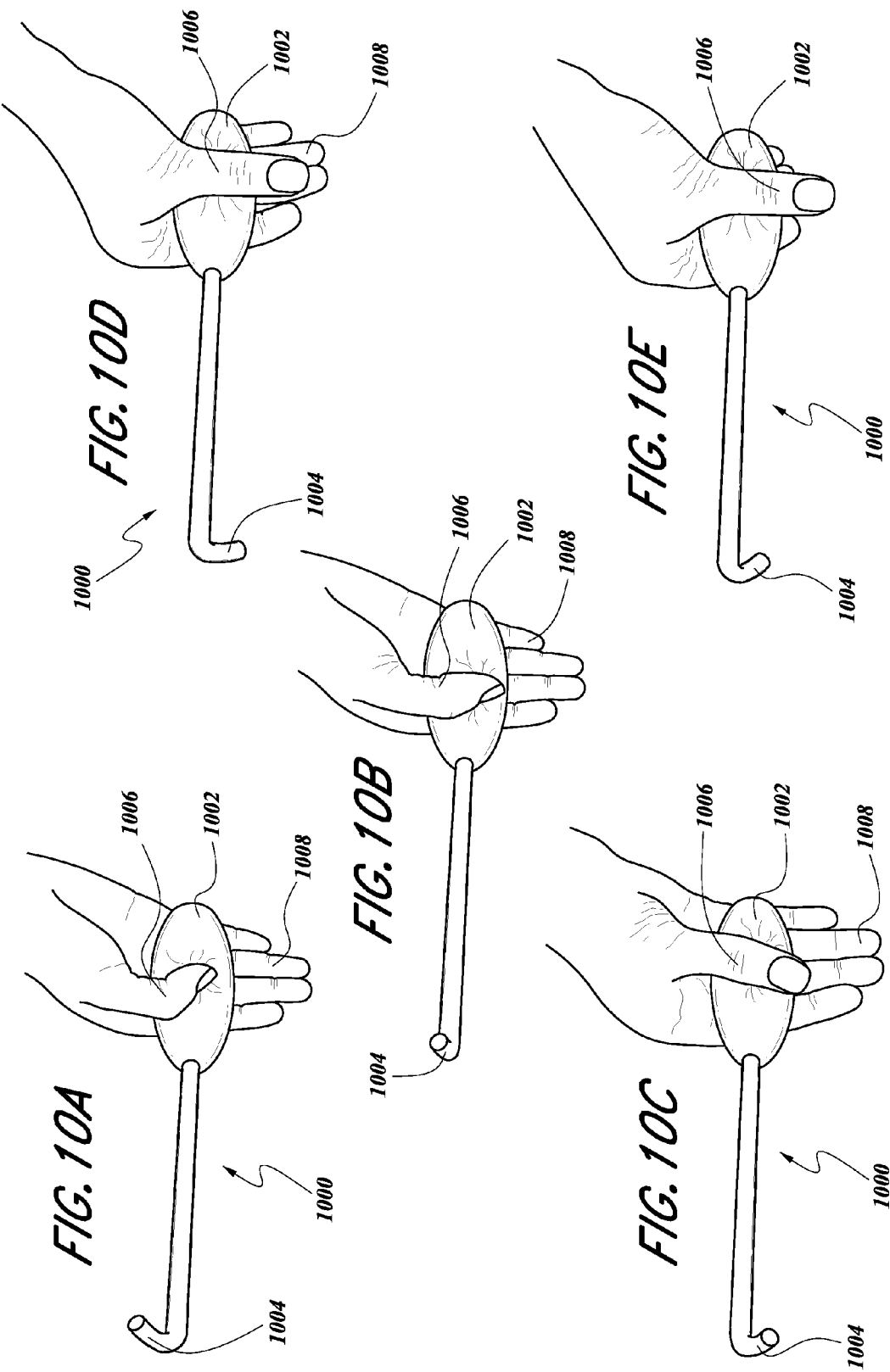

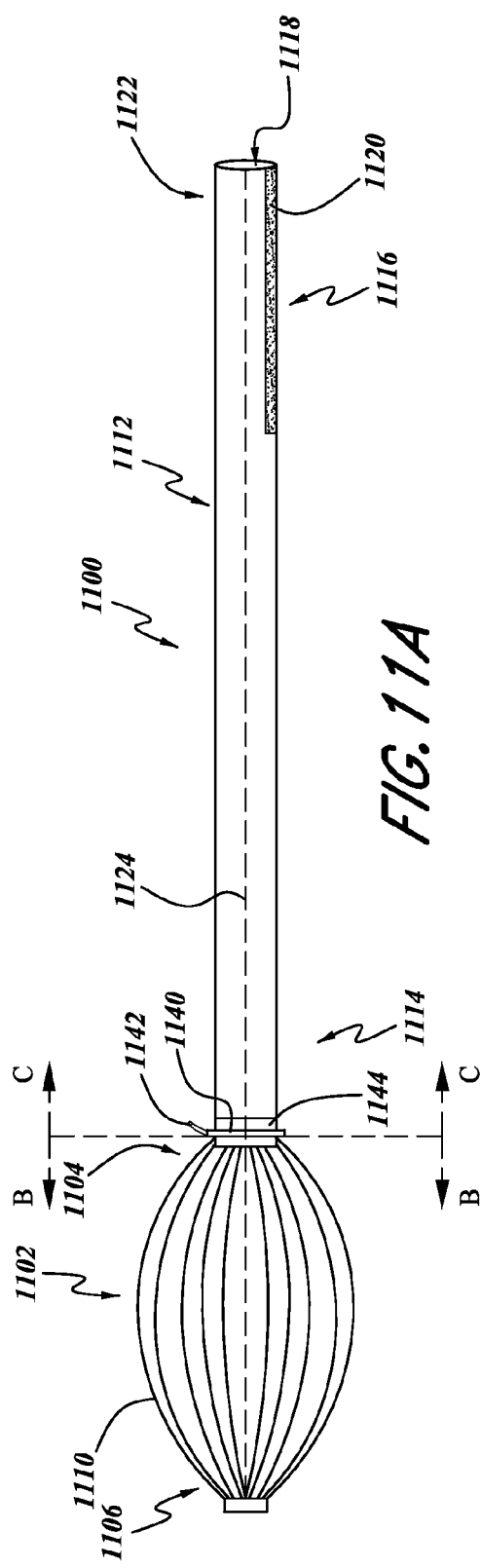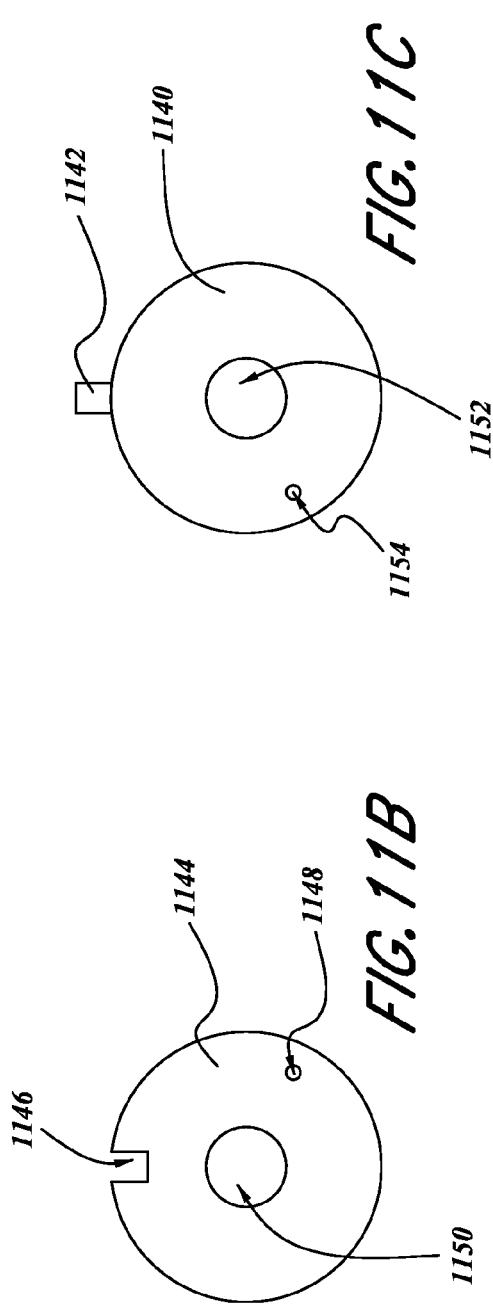

STEERABLE CATHETERS

FIELD

The present application relates generally to steerable catheters.

BACKGROUND

Catheters are routinely used in medical procedures and serve various functions, including drainage, administration of fluids or gases, allowing surgical instruments access to treatment sites, etc. A catheter can be inserted into a body lumen through the skin or percutaneously. The catheter is then guided to an area of interest by advancing the catheter through the lumen. As medical technology advances, catheters are being used for more and more complicated procedures. Accurate navigation of the catheter to a particular luminal position can be useful for successful treatment.

SUMMARY

In some embodiments, a steerable catheter comprises a handle at a proximal portion of the steerable catheter, the handle including a proximal end, a distal end, and an axis between the proximal end of the handle and the distal end of the handle. The handle comprises a plurality of resilient metal strips coupled at the proximal end of the handle and at the distal end of the handle, the metal strips biased into an arcuate configuration, the metal strips extending away from the axis from the proximal end of the handle to an intermediate point along the handle and the metal strips extending towards the axis from the intermediate point to the distal end of the handle. The handle comprises a cover over the plurality of resilient metal strips. The catheter also comprises an elongate tubular body, the tubular body including a proximal portion and a distal portion. The proximal portion is coupled to the distal end of the handle. The distal portion includes a distal end of the tubular body. A plurality of lumens extends from the proximal portion to the distal portion. The distal portion comprises a shape-memory ribbon longitudinally extending along the tubular body proximate to the distal end of the tubular body. The steerable catheter comprises a pull wire extending from the proximal end of the handle to the distal end of the tubular body through one lumen of the plurality of lumens, a second lumen of the plurality of lumens configured to provide a path for an endoluminal device. Upon manual inward compression of at least some of the resilient metal strips, the at least some of the resilient metal strips compress from the arcuate configuration to a straighter configuration, a degree of straightening corresponding to a force applied during the manual inward compression of the at least some of the resilient metal strips. The proximal end of the handle and the pull wire extend proximally, a degree of proximal extension corresponding to the force applied during the manual inward compression of the at least some of the resilient metal strips. The distal portion of tubular body deflects from a substantially straight configuration to a curved configuration, a degree of deflection corresponding to the force applied during the manual inward compression of the at least some of the resilient metal strips. Upon manual decompression of the at least some of the resilient metal strips, the at least some of the resilient metal strips rebound towards the arcuate configuration, a degree of rebounding corresponding to a force of the manual decompression of the at least some of the resilient metal strips. The proximal end of the handle and the pull wire extend distally, a degree of distal extension corresponding to the force of the manual decompression of the at least some of the resilient metal strips. The shape-memory ribbon deflects the distal portion of the tubular body from the curved configuration to the substantially straight configuration, a degree of uncurling corresponding to the force of the manual decompression of the at least some of the resilient metal strips. Upon rotation of the handle about the axis, the distal end of the tubular body rotates. The handle is rotatable at least 360° about the axis by rolling between a thumb and fingers of a user.

In some embodiments, a steerable catheter comprises a handle including a proximal end, a distal end, and an axis between the proximal end of the handle and the distal end of the handle. The handle comprises comprising a plurality of resilient and flexible struts coupled at the proximal end of the handle and at the distal end of the handle. The struts are biased into an elliptical configuration, extending away from the axis from the proximal end of the handle to an intermediate point along the handle and the struts extending towards the axis from the intermediate point to the distal end of the handle. The steerable catheter also comprises an elongate tubular body including a proximal portion and a distal portion. The proximal portion is coupled to the distal end of the handle. The distal portion includes a distal end of the tubular body. A lumen extends from the proximal portion to the distal portion. The distal portion comprises a resilient component. The catheter comprises a pull wire extending from the proximal end of the handle to the distal end of the tubular body through the lumen. The pull wire is configured to extend proximally upon inward compression of the handle proportional to a force of the inward compression. The distal portion is configured to curve upon inward compression of the handle proportional to the force of the inward compression. The handle is rotatable at least 360° about the axis by rolling between a thumb and fingers of a user.

The struts can comprise a wire or ribbon. In some embodiments the struts comprise nitinol. The handle can comprise a cover over the plurality of struts. In some embodiments, the resilient component comprises a longitudinally extending ribbon. The resilient component can comprise a shape memory material. In some embodiments, the catheter comprises a second lumen configured to provide a path for an endoluminal device. Upon manual decompression, the pull wire can be configured to retract distally proportional to a force of the decompression and the distal portion of the tubular body can be configured to straighten upon decompression of the handle proportional to the force of the decompression. The catheter can comprise a second pull wire extending from the proximal end of the handle to the distal end of the tubular body. The second pull wire can be configured to extend proximally upon inward compression of a second part of the handle proportional to a force of the inward compression and the distal portion of the tubular body can be configured to curve in a second direction different than the first direction upon inward compression of the second part of handle proportional to the force of the inward compression. The first and second pull wire can be coupled to the distal end of the tubular body at pull wire fix points, the pull wire fix points spaced circumferentially around a circumference of the tubular body proximate to the distal end of the tubular body. The catheter can comprise a locking mechanism configured to maintain the pull wire in an extended configuration.

In some embodiments, a method of using a steerable catheter comprises advancing a handle, the handle coupled to an elongate tubular body in a lumen, the handle comprising a proximal end, a distal end, and an axis between the proximal end of the handle and the distal end of the handle. The handle comprises a plurality of resilient and flexible struts biased into an arcuate configuration, the struts coupled at the proximal end of the handle and the distal end of the handle, the struts extending away from the axis from the proximal end of the handle to an intermediate point along the handle and the struts extending towards the axis from the intermediate point to the distal end of the handle. The elongate tubular body comprises a proximal portion and a distal portion, the proximal portion coupled to the distal end of the handle, the distal portion including a distal end of the tubular body. The distal portion comprises a resilient component longitudinally extending along the tubular body proximate to the distal end of the tubular body. The elongate tubular body comprises a lumen extending from the proximal portion to the distal portion and a pull wire extending from the proximal end of the handle to the distal end of the tubular body within the lumen. The method further comprises manually inwardly compressing the handle, extending the proximal end of the handle and the pull wire proximally and deflecting the distal end of the tubular body from a substantially straight configuration to a curved configuration. A degree of deflecting corresponds to a force applied during the manual inward compression.

In some embodiments, the method further comprises rotating the handle of the catheter, the distal end of the elongate member rotating during or after manually inwardly compressing the handle. Rotating the handle of the catheter comprises rotating the handle between a thumb and fingers of a user of the catheter. In some embodiments, the method comprises manually decompressing the handle, the handle rebounding towards an unbiased configuration, the proximal end of the handle and the pull wire retracting distally, and deflecting the distal end of the tubular body from a curved configuration to the substantially straight configuration, a degree of deflection corresponding to a force of manual decompression of the handle. The method can comprise locking the pull wire in a proximally extended configuration.

For purposes of summarizing the invention and the advantages achieved over the prior art, certain objects and advantages are described herein. Of course, it is to be understood that not necessarily all such objects or advantages need to be achieved in accordance with any particular embodiment. Thus, for example, those skilled in the art will recognize that the invention may be embodied or carried out in a manner that can achieve or optimize one advantage or a group of advantages without necessarily achieving other objects or advantages.

All of these embodiments are intended to be within the scope of the invention herein disclosed. These and other embodiments will become readily apparent to those skilled in the art from the following detailed description having reference to the attached figures, the invention not being limited to any particular disclosed embodiment(s).

BRIEF DESCRIPTION OF THE FIGURES

These and other features, aspects, and advantages of the present disclosure are described with reference to the drawings of certain embodiments, which are intended to illustrate certain embodiments and not to limit the invention.

FIG. 2 illustrates the steerable catheter of FIG. 1 in another configuration.

FIG. 3 illustrates the steerable catheter of FIG. 2 in another configuration.

FIG. 4 schematically illustrates another example embodiment of a steerable catheter.

FIG. 5 illustrates the steerable catheter of FIG. 4 in another configuration.

FIG. 6 schematically illustrates another example embodiment of a steerable catheter.

FIG. 7 illustrates the steerable catheter of FIG. 6 in another configuration.

FIG. 8 schematically illustrates another example embodiment of a steerable catheter.

FIG. 9 illustrates the steerable catheter of FIG. 8 in another configuration.

FIGS. 10A-10I illustrate an example embodiment of a method for using a steerable catheter.

FIG. 11A schematically illustrates another example embodiment of a steerable catheter.

FIG. 11B is a cross-sectional view of the steerable catheter of FIG. 11A along the line B-B.

FIG. 11C is a cross-sectional view of the steerable catheter of FIG. 11A along the line C-C.

DETAILED DESCRIPTION

Figure 1:
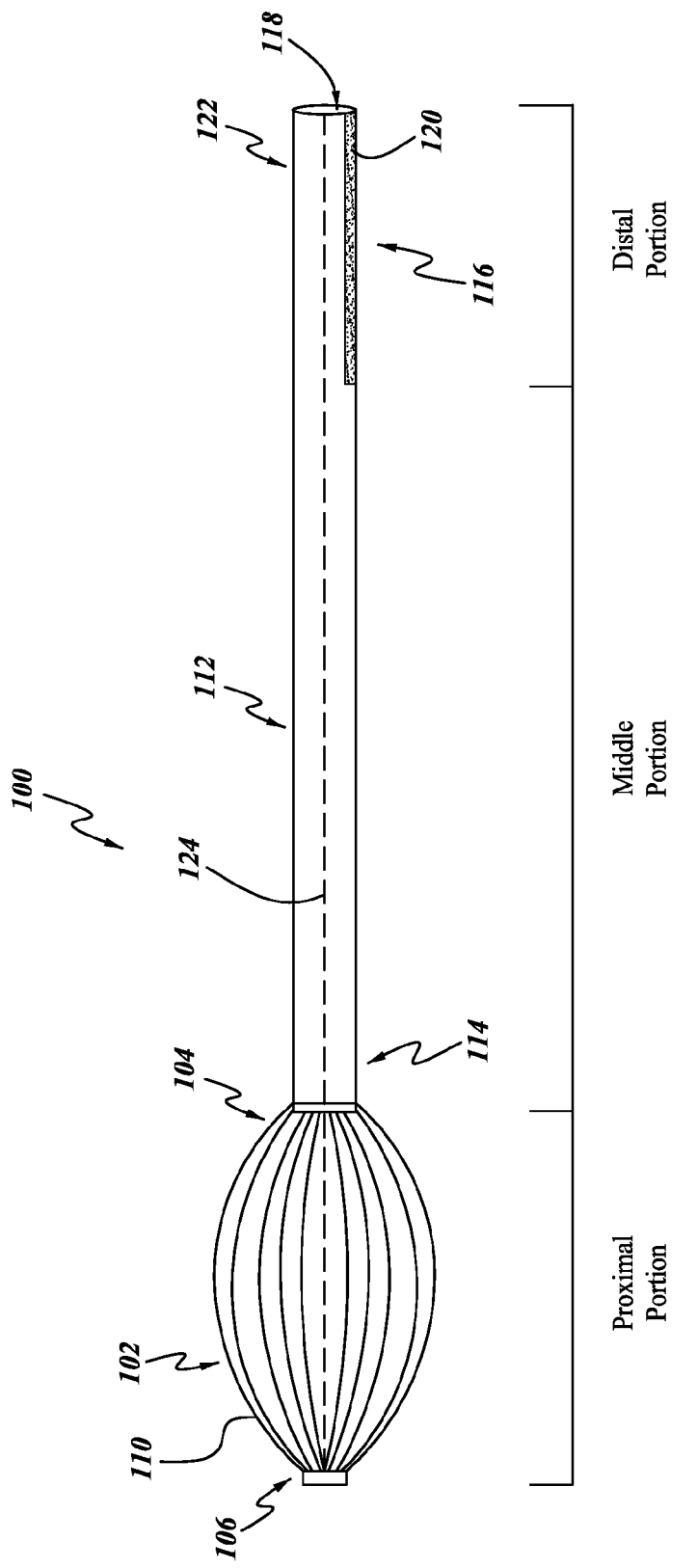
FIG. 1 schematically illustrates an example embodiment of a steerable catheter.

Although certain embodiments and examples are described below, those of skill in the art will appreciate that the invention extends beyond the specifically disclosed embodiments and/or uses and obvious modifications and equivalents thereof. Thus, it is intended that the scope of the invention herein disclosed should not be limited by any particular embodiments described below.

Example steerable catheters are provided, each including a handle and an elongate tubular portion. The handle includes multiple segments (e.g., strips, wires), connected at a proximal end of the handle and a distal end of the handle. The segments form a generally arcuate shape such as a sphere or an ellipse. The tubular portion is connected to the distal end of the handle. The tubular portion includes a resilient component positioned near a distal tip of the tubular portion. The resilient component can include a shape-memory material and can extend longitudinally along the tubular portion near the distal tip of the tubular portion. The catheter includes a pull wire fixed to a point near the distal tip of the tubular portion and fixed to a point near the proximal end of the handle. Upon manual compression or squeezing of the handle, the segments are squeezed together, causing the shape of the handle to flatten and lengthen. As the handle lengthens, the pull wire, fixed to the proximal end of the handle, is pulled back, away from the tubular portion. This retraction of the pull wire pulls on the distal tip of the tube portion at the point where the pull wire is fixed to the distal tip of the tubular portion, causing the distal tip of the tubular portion to deflect away from the longitudinal axis of the tubular portion. The deflection may take the form of curvature of the distal tip of the tubular portion. The amount of deflection is proportional to the amount of compression or squeezing of the handle. Increasing the squeezing or compressing of the handle increases the retraction of the pull wire and the deflection of the distal tip. Decreasing the squeezing or compressing of the handle decreases the retraction of the pull wire and the deflection of the distal tip. Upon decompression or release of the handle, the segments of the handle return towards their arcuate configuration and the pull wire moves distally. When no other forces are acting on the resilient component at the distal tip of the tubular member, the resilient component can return to its original configuration, which is usually straight but may also be curved (e.g., curved in the opposite direction to the direction of deflection), and the distal tip can follow the shape of the resilient component. The amount of rebounding is proportional to the amount of decompression or release of the handle. Increasing the decompression or release of the handle increases the distal movement of the pull wire and the amount of rebounding of the distal tip of the tubular portion. Decreasing the decompression or release of the handle decreases the distal movement of the pull wire and the amount of rebounding of the distal tip of the tubular portion. Alternative handles (e.g., including one or more compressible buttons), tubular portions, and other components are also disclosed.

FIG. 1 schematically illustrates an example embodiment of a steerable catheter 100. The steerable catheter comprises a handle 102 positioned at a proximal end of the steerable catheter 100. The handle 102 comprises a proximal end 106 and a distal end 104. An axis (not shown) extends between the proximal end 106 and the distal end 104. The handle comprises a plurality of struts 110 coupled at the proximal end 106 of the handle 102 and at the distal end 104 of the handle 102. The struts 110 may be biased into an arcuate (e.g., elliptical, spherical, etc.) configuration, as shown in FIG. 1. The struts 110 may extend away from the axis from the proximal end 106 of the handle 102 to an intermediate point along the handle 102. The struts 110 may extend towards the axis from the intermediate point to the distal end 104 of the handle 100.

The steerable catheter 100 comprises an elongate tubular body 112 positioned distally of the handle 102. The elongate tubular body 112 comprises a proximal portion 114 and a distal portion 116. A lumen 118 extends from the proximal portion 114 to the distal portion 116. The distal portion 116 of the tubular body 112 comprises a resilient component 120. The resilient component 120 is positioned at or near the distal end 122 of the tubular body 112. The resilient component 120 may extend proximally from a point at or near the distal end 122 of the tubular body 112. In some embodiments, the elongate tubular body 112 is more malleable towards the distal end 122 of the tubular body 112 than towards the proximal end 114 of the tubular body. This increased malleability can allow enhanced bendability around tortuous anatomy.

The steerable catheter 100 comprises a pull wire 124 extending from the proximal end 106 of the handle 102 to the distal end 122 of the tubular body 112. The pull wire 124 is connected to the handle 102 at or near the proximal end 106 of the handle and is connected to the elongate tubular body 112 at or near the distal end 122 of the body 112.

FIG. 2 depicts the steerable catheter 100 with the distal portion 116 of the tubular body in a deflected position. The handle 102, including the plurality of struts 110, is configured to be compressible by a hand of a user. A user may compress the handle within their hand, compressing at least some of the struts 110. The compression is shown as inward pointing arrows 130 around the handle 102 in FIG. 2. In some embodiments, the user compresses all of the struts 110. In some embodiments, the user compresses only some of the struts 110. Upon manual inward compression of at least some of the struts 110, the struts 110 compress from an elliptical or arcuate configuration to a straighter configuration.

The degree of straightening of the struts 110 may correspond to the force applied during the manual inward compression of the at least some of the resilient metal struts. For example, increasing the force applied during compression of the struts 110 can increase the degree of straightening. Conversely, decreasing the force applied during compression of the struts 110 can decrease the degree of straightening.

Compressing the handle 102 may proximally extend the proximal end 106 of the handle 102, pulling the pull wire 124 proximally, as shown by the proximally pointing arrow 132 in FIG. 2. The degree of the proximal extension of the proximal end 106 of the handle 102 and the pull wire 124 may correspond to the force applied during the manual inward compression of at least some of the struts 110. For example, increasing the force applied to the struts 110 can increase the proximal extension of the proximal end 106 of the handle 102 and the pull wire. Conversely, decreasing the force applied during manual inward compression of the struts 110 can decrease the proximal extension of the proximal end 106 of the handle 102 and the pull wire 124.

Proximal extension of the pull wire 124 at the distal end 122 of the tubular body causes deflection of the distal portion 116 of the tubular body 112, shown by the arrow 134 in FIG. 2. The degree of deflection may correspond to the force applied during the manual inward compression of at least some of the struts 110. For example, increasing the force applied to the struts 110 can increase the deflection of the distal portion 116 of the tubular body 112. Conversely, decreasing the force applied during manual inward compression of the struts 110 can decrease deflection of the distal portion 116 of the tubular body 112.

The distal portion 116 that curves may be defined between the distal end 122 of the catheter 100 and the proximal end of the resilient component 120. The distal portion 116 may be capable of curving up to 180° within the plane of curvature. The plane of curvature may be a plane including the resilient portion 120 and a section extending along the tubular body 112 that is generally opposite from the resilient portion 120.

FIG. 3 depicts the catheter 100 after decompression of the handle 102. Decompression of the struts 110 may cause the struts 110 to rebound towards the arcuate configuration, as shown by the outward pointing arrows 136 in FIG. 3. The degree of rebounding of the struts 110 may correspond to the force applied during the manual inward decompression (e.g., the force applied when releasing at least some of the struts) of the at least some of the resilient metal struts. For example, increasing the force applied during decompression of the struts 110 can increase the degree of rebounding. Conversely, decreasing the force applied during decompression of the struts 110 can decrease the degree of rebounding.

Decompression of the handle 102 causes distal retraction of the proximal end 106 of the handle 102, shown as distally pointing arrow 138 in FIG. 3, allowing the pull wire 124 to retract distally. The degree of the distal retraction of the proximal end 106 of the handle 102 and the pull wire 124 may correspond to the force applied during the decompression of the struts 110. For example, increasing the force applied during decompression of the struts 110 can increase the distal retraction of the proximal end 106 of the handle 102 and the pull wire. Conversely, decreasing the force applied during manual inward compression of the struts 110 can decrease the proximal retraction of the proximal end 106 of the handle 102 and the pull wire 124.

Distal retraction of the pull wire 124 allows the distal portion 116 of the tubular body to rebound from a deflected or curved configuration towards a straighter configuration, shown by arrow 140 in FIG. 3. Distal retraction of the pull wire 124 decreases the deflecting force applied to the resilient component 120. With less deflecting force acting upon the resilient component 120, it rebounds to its original (e.g., straight) position. The degree of rebounding of the distal portion 116 may correspond to a force applied during decompression of the handle 102. For example, increasing the force applied during decompression of the struts 110 can increase the rebounding of the distal portion 116. Decreasing the force applied during decompression of the struts 110 can decrease rebounding of the distal portion 116.

The deflection and rebounding of the distal portion 116 of the tubular body 112 can allow the catheter 100 to be navigated through tortuous sections of the anatomy (e.g., the vasculature). This ability to navigate can allow the catheter 100 to be used as a guiding catheter for use in peripheral vasculature or coronary sinus areas, implant delivery systems, and for EP mapping, among other applications. Many steerable catheters currently available use some sort of handle, lever, or motor/switch system by which they cause the distal end of the catheter to curve. Such configurations do not allow for optimal control over the steering or provide tactile feedback to the physician attempting to steer the catheter. Furthermore, some "digital" steering mechanisms do not provide any tactile feedback or allow for fine control in response to the anatomy encountered during a medical procedure. This compression and decompression can be described as "analog" because there are an infinite number of positions the pull wire can be extended to and an infinite number of curvatures that can be imparted to the distal portion. By contrast, existing structures can generally only be operated in two "digital" predetermined curvatures (one of which may be no curvature). In the case of currently available "analog" steering mechanisms, one finger or thumb is generally used to steer the catheter, which provides less than ideal tactile feedback and can be difficult to control consistently. In contrast, the steering mechanism disclosed herein is controlled by an analog, compressible handle 102 configured to be grasped by the hand (e.g., thumb, palm, and at least some fingers) of a user. Parts of the hand working together can allow for increased tactile feedback and control over currently available systems.

In some embodiments, the catheter 100 comprises more than one lumen extending from the proximal portion 114 to the distal portion 116. The pull wire may be housed within a "false" lumen. The catheter may also comprise one or more working or functional lumens. For some examples, a guidewire, other catheters, devices (e.g., endoluminal devices), therapeutic agents, or a wire for EP applications could be navigated through these working or functional lumens. The lumens may be side-by-side, coaxial, round, partially round (e.g., wedges, semicircular, crescent, etc.).

In some embodiments, the struts 110 comprise a wire. Other shapes for the struts are also possible. For example, in some embodiments, the struts 110 comprise a ribbon. In some embodiments, all of the struts 110 comprise a same shape. In other embodiments, the struts 110 comprise different shapes. For example, some of the struts 110 may comprise a wire and others of the struts 110 may comprise a ribbon.

The struts 110 comprise a resilient and flexible material. In some embodiments, the struts 110 comprise a shape memory material. In some embodiments, the struts 110 comprise a metal. The struts 110 may comprise a nickel-titanium alloy (e.g., Nitinol). In some embodiments, the struts 110 comprise a polymer (e.g., carbon fiber). Other resilient and flexible materials are also possible. In some embodiments, the struts 110 comprise the same material. In some embodiments, the struts 110 comprise different materials. For example, some (e.g., half) of the struts may comprise Nitinol, and the remaining struts 110 may comprise carbon fiber, stainless steel, etc. For another example, one strut of the plurality of struts 110 may comprise Nitinol, and the remainder of the struts 110 may comprise carbon fiber, stainless steel, etc.

In some embodiments, the handle 102 comprises a cover over the plurality of struts 110. A cover positioned over the handle 102 can enhance the ease of use and comfort of the handle 102 for a user. For example, the cover can prevent pinching of the user's hands upon movement of the strips. The cover can also provide a textured surface that is easier to manipulate than the strips. In some embodiments, the cover comprises silicone. Other materials (e.g., other polymers and plastics) are also possible.

In some embodiments, the resilient component 120 comprises a shape memory material. For example, the resilient component 120 can comprise a nickel titanium alloy (e.g., Nitinol). In some embodiments, the resilient component 120 comprises a ribbon. Other shapes are also possible. For example, the resilient component 120 can comprise a wire. Other materials comprising rebound tensile strength (e.g., springs) are also possible. In some embodiments, the resilient component 120 is continuous along a portion of the tubular body 112. In some embodiments, the resilient component comprises multiple discrete components within the tubular body 112. In some embodiments, the catheter 100 comprises multiple resilient components 120. In some embodiments, a number, shape, and material of resilient components can be used to affect a rigidity of the catheter 100. For example, multiple resilient components or a more rigid material in the resilient component can involve a greater compressive force on the handle of the catheter to deflect the distal portion 116 of the catheter 100.

In some embodiments, the resilient portion 120 is pre-curved in a first direction by curving the resilient component 120. In such embodiments, compressing the handle 102 causes the distal portion 116 of the catheter to curve in a second direction, which may be opposite to the first direction. In embodiments comprising a pre-curved resilient portion 120, curvature of the distal portion 116 up to 360° within the plane of curvature may be possible.

FIG. 4 schematically illustrates another example embodiment of a steerable catheter 400. Unless otherwise noted, the catheter 400 comprises features similar to the catheter described with respect to FIGS. 1-3. The catheter 400 comprises a handle 402 comprising a depressable portion or bump 404. The depressable portion or bump 404 is connected to a pull wire 424 extending from the bump 404 to a distal end 422 of the catheter 400. The catheter 400 comprises a pulley or rod 406, on which the pull wire 424 rests. Like the catheter 100 shown in FIG. 1, the catheter 400 comprises a resilient portion 420 at the distal end 422 of the catheter 400.

A finger may be used to depress the bump 404. For example, the thumb or index finger may be used to depress the bump 404, which may allow for greater accuracy and tactile feedback than using other fingers or an entire hand.

FIG. 5 depicts the catheter 400 while the bump 404 is being depressed, shown by arrow 430 in FIG. 5. Depression of the bump 404 causes proximal extension of the pull wire 424 around the pulley 406 and down. A degree of proximal extension of the pull wire corresponds to the downward extension of the bump 404 and the downward extension of the pull wire 424 around the pulley 406. Increasing the downward extension of the pull wire 424 around the pulley 406 may increase the proximal extension of the pull wire 424. Proximal extension of the pull wire 424 at the distal end 422 of the catheter 400 causes deflection of a distal portion 416 of the catheter 400, shown by arrow 434. A degree of deflection corresponds to a force applied during depression of the bump 404, for example as described with respect to catheter 100. Increasing the proximal extension of the pull wire 424 (e.g., by increasing the downward extension of the bump 404) can increase the deflection of the distal portion 416 of the catheter 400.

Release of the bump 404 can cause distal retraction of the pull wire 424 and allow rebounding of the distal portion 416 of the catheter 400, for example as described above with respect to the catheter 100. Distal retraction of the pull wire 424 decreases the deflecting force applied to the resilient component 420. With less deflecting force acting upon the resilient component 420, it rebounds to its original (e.g., straight) position. In some embodiments, the catheter 400 comprises a resilient component (e.g., a spring) below the bump 404. In such an embodiment, the downward extension of the bump 404 may cause proximal extension of the pull wire 424, as described above. Upon release of the bump 404, the resilient component may cause the bump 404 to rebound towards its original position, which may retract the pull wire 424 and may cause the distal portion 416 to return to a straighter configuration. In certain such embodiments, the catheter 400 optionally does not include a resilient component at its distal end, as the resilient component at the bump 404 may control the rebounding.

In some embodiments, the catheters disclosed herein comprise multiple pull wires. For example the catheters can comprise 1, 2, 3, 4, or more pull wires. The pull wires can be connected to pull wire fix points near or at the distal end of the catheter. In some embodiments, the pull wire fix points can be spaced circumferentially around a circumference of the tubular body (e.g., 112 proximate to the distal end 122 of the tubular body 112). In such embodiments, the different pull wires may be used to deflect the catheter in different directions.

FIG. 6 schematically illustrates an example embodiment of a steerable catheter 600. The catheter 600 is similar to the catheter 400, shown in FIGS. 4 and 5, but the catheter 600 comprises a handle 602 comprising a first bump 604 and a second bump 605. The catheter 600 also comprises a first pull wire 624 and a second pull wire 625. The catheter 600 optionally comprises a resilient component 620 positioned at a distal portion 616 of the catheter 600. The multiple pull wires with separate controls can allow for deflection of the distal portion 616 of the catheter 600 in multiple directions.

As shown in FIG. 6, depressing the top bump 604 extends the top pull wire 624 proximally and around the top pulley or rod 606. The proximal extension of the pull wire 624 at the distal end 622 of the catheter 600 causes the distal portion 616 of the catheter 600 to deflect upwards shown by arrow 630 in FIG. 6.

Releasing the bump 604 causes the pull wire 624 to move upwards around the pulley 606, and can cause distal retraction of the pull wire 624. The distal retraction of the pull wire 624 can cause the distal portion 616 of the catheter 600 to rebound towards a straighter configuration. The rebounding may be caused by a resilient component positioned at the distal portion 616 of the catheter 600. In some embodiments, the rebounding may be caused by a resilient component under the bump 604. In some embodiments, the rebounding may be caused by deflecting the pull wire 624 in a different direction by pressing the bump 605, as described below.

FIG. 7 illustrates the catheter 600 when the bottom bump 605 is depressed. Depressing the bottom bump 605 extends the bottom pull wire 625 proximally and upwards around the bottom pulley or rod 607. The proximal extension of the pull wire 625 at the distal end 622 of the catheter 600 causes the distal portion 616 of the catheter 600 to deflect downwards shown by arrow 632 in FIG. 7. Releasing the bump 605 can cause the pull wire 625 to move downwards around the pulley 607, retracting the pull wire 625 distally. Distal retraction of the pull wire 625 can cause the distal portion 616 of the catheter 600 to rebound towards a straighter configuration. The rebounding may be caused by a resilient component positioned at a distal portion 616 of the catheter 600. The rebounding may be caused by a resilient component above the bump 607. In some embodiments, the rebounding may be caused by deflecting the pull wire 625 in a different direction by pressing the bump 604.

In some embodiments, the catheter comprises more than two bumps and two pull wires, which can allow the distal end of the catheter to be steered by deflecting the distal portion in additional directions without rotation of the catheter. It will be appreciated that the bumps can comprise different shapes than those shown in FIGS. 6 and 7.

FIG. 8 schematically illustrates another example embodiment of a steerable catheter 800. The catheter 800 comprises a handle 802, for example similar to that described with respect to the catheter 100 of FIGS. 1-3. The handle 802 comprises a proximal end 806 and a distal end 804. The handle 802 comprises a plurality of struts 810 coupled at the proximal end 806 of the handle 802 and at the distal end 804 of the handle 802. The struts 810 may be biased into an arcuate (e.g., elliptical, spherical, etc.) configuration. The struts 810 extend away from the axis from the proximal end 806 of the handle 802 to an intermediate point along the handle 802. The struts 810 extend towards the axis from the intermediate point to the distal end 804 of the handle 800.

The steerable catheter comprises an outer elongate body 812 and an inner elongate body 813. A proximal end of the outer elongate tubular body 812 may be connected to the proximal end 806 of the handle 802. A proximal end of the inner elongate tubular body 813 may be connected to the distal end 804 of the handle 802. The outer elongate tubular body 812 may include slits (not shown) that allow the struts 810 to be connected to the inner elongate tubular body through the outer body 812. A distal portion 816 of the inner body 813 may be pre-shaped in a particular configuration (e.g., curved). The distal portion 816 of the tubular body 813 may comprise a resilient component (not shown), for example similar to any of the resilient components 120, 420, 620, that has been pre-shaped. The distal portion 816 may be housed within the straight outer body 812.

FIG. 9 shows the catheter 800 during compression of the handle 802. Compression of the handle 802 or at least some of the struts 810 can proximally extend the proximal end 806 of the handle proximally, as shown by arrow 830 in FIG. 9. The proximal extension of the distal end 806 of the handle 802 may cause the outer tubular body 812 to extend proximally. The inner body 813, which is not connected to the proximal end 806 of the handle 802, does not extend proximally along with the outer body 812. The proximal movement of the outer tubular body 812 may cause the distal portion 816 of the inner tubular body 813 to emerge or prolapse from the distal end of the outer body 812. Without the outer tubular body 812 biasing the distal portion 816 of the inner tubular body 813 into a straight configuration, the distal portion 816 can return to its pre-shaped configuration, as shown by arrow 832.

Decompression of the handle 802 allows the proximal end 806 of the handle 802 to retract distally. Decompression of the handle 802 causes at least some of the struts 810 to return to a straighter configuration. Some of the struts 810 returning to a straighter configuration can cause the proximal end 806 of the handle 802 to retract distally. The distal retraction of the proximal end 806 of the handle 802 causes the outer tubular body 812 to retract distally. The distal retraction of the outer tubular body causes the inner tubular body 813 to be sheathed within the outer tubular body 812, causing the distal portion 816 to return to a straight configuration.

Configurations for the pull wire and sleeve other than those shown in FIGS. 8 and 9 are also possible. For example, in some embodiments, instead of retracting the outer tubular body, the inner tubular body may be pushed out of the outer body, which may also cause the distal portion of the inner body to return to its pre-shaped configuration. It will be appreciated that, in some embodiments, the sleeve and the inner catheter can be fixed using other fixation modalities. For example, a pull wire may connect the outer catheter to the proximal end of the handle. Metal strips, plastic strips, or tubes may also be used. For another example, the sleeve may be directly fixed to the proximal end of the grip. Other configurations are also possible.

FIGS. 10A-10I schematically illustrate an example embodiment of a method of rotating a catheter 1000 comprising a handle 1002 similar to the handles (e.g., handles 102, 802) described above. Once the catheter 1000 has been advanced to a location requiring steering of the catheter, the handle 1002 is squeezed. As described above with respect to the catheter 100, compression of the handle 1002 causes the pull wire, which is fixed to the proximal end of the handle 1002, to extend proximally, deflecting the distal tip 1004 of the catheter. As described above with respect to the catheter 800, compression of the handle 1002 causes the outer tube, which is fixed to the distal end of the handle 1002, to extend proximally and allow prolapse of the inner tube, deflecting the distal tip 1004 of the catheter. In some embodiments, for example, when navigating through tortuous anatomy (e.g., the vasculature), after deflecting the distal tip 1004 of the catheter 1000, the anatomy may require the user to steer the catheter 1000 in another direction. Rotating the catheter 1000 around a longitudinal axis by rotating the handle 1002 can allow the user to steer the catheter 1000 in a different direction with the distal tip 1004 in a curved configuration.

FIG. 10A depicts the handle 1002 being squeezed between the thumb 1006 and the fingers 1008 of the user, causing the distal tip 1004 to deflect. Other configurations for squeezing the handle 1002 are also possible. For example, a user may squeeze the handle 1002 with a palm or the arch between the thumb and the index finger. In FIG. 10B, the user maintains pressure on the handle 1002, keeping the distal tip 1004 deflected, and moves the thumb 1006 forward (or downward as shown on the page) and/or moving the fingers 1008 backwards (or upward as shown on the page). FIGS. 10C-10E show the thumb 1006 continuing to move forwards and/or the fingers 1008 continuing to move backwards, or a combination thereof. As the handle 1002 rotates within the hand of the user, the distal tip 1004 of the catheter 1000 also rotates. It will be appreciated that the user can rotate the handle 1002 in various ways. For example, the user my instead extend the fingers while retracting the thumb.

In some embodiments, the catheter is sufficiently rigid for the distal tip 1004 of the catheter to equally match the rotation of the handle 1002. In some embodiments, the distal tip 1004 of the catheter 1000 does not rotate at the same rate as the handle 1002.

Figure 10F:
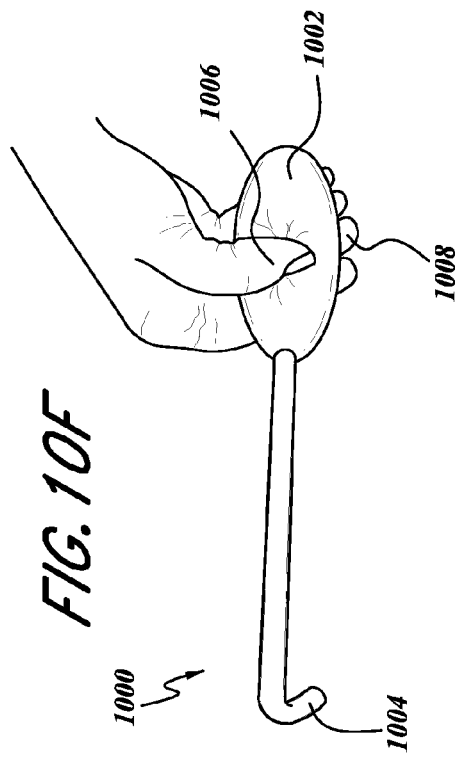
Figure 10G:
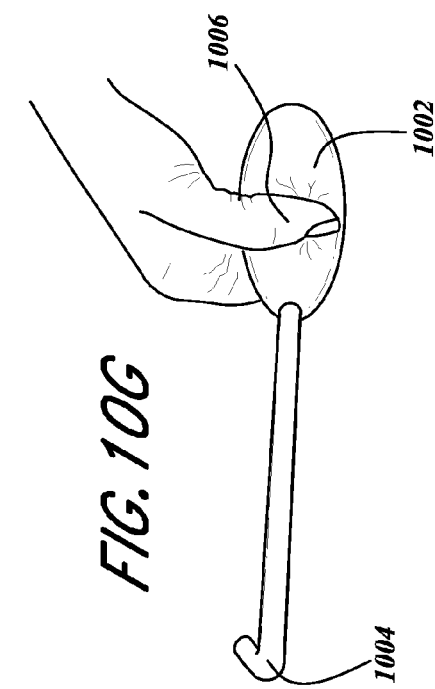
Figure 10H:
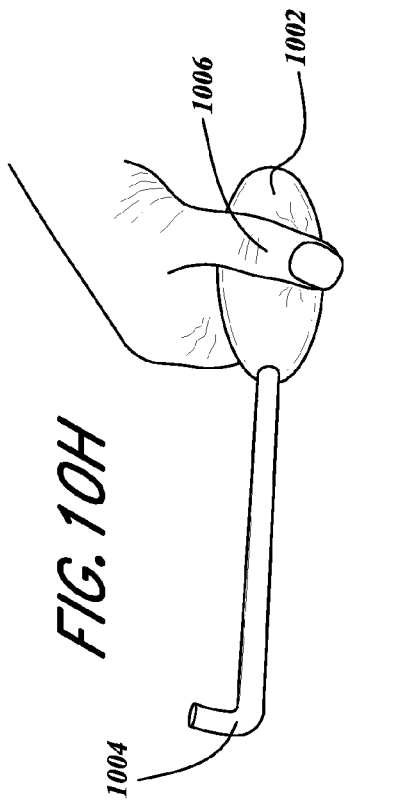
Figure 10I:
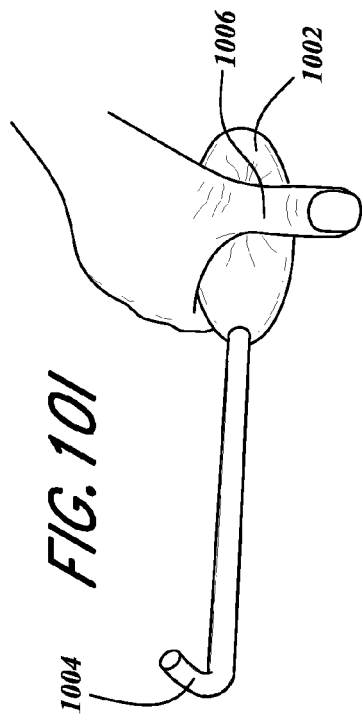

FIG. 10F depicts the user maintaining pressure on the handle 1002 using the fingers 1008, but moving the thumb backwards to allow for further rotation. The thumb 1006 is now in a similar position as was shown in FIG. 10A. FIGS. 10G-10I depict the thumb 1006 extending and/or the fingers 1008 retracting, rotating the catheter 1000, including the distal tip 1004. As shown in FIGS. 10A-10I, the catheter 1000 is capable of at least 360° of rotation. Using the method depicted in FIGS. 10A-10I, the catheter 1000 can be rotated greater than 360°. Although shown in FIGS. 10A-10I as always being in a substantially similar curved configuration throughout the rotation, the distal tip 1004 may be further curved and/or straightened during the rotation, for example based on tactical sensation.

FIG. 11A schematically illustrates an example embodiment of a catheter 1100 comprising an optional locking mechanism. Unless otherwise described, the catheter 1100 is similar to the catheter 100 described with respect to FIG. 1. The catheter 1100 comprises a handle 1102 positioned at a proximal end of the steerable catheter 1100. The handle 1102 comprises a proximal end 1106 and a distal end 1104. An axis (not shown) extends between the proximal end 1106 and the distal end 1104. The handle comprises a plurality of struts 1110 coupled at the proximal end 1106 of the handle 1102 and at the distal end 1104 of the handle 1102. The struts 1110 may be biased into an arcuate (e.g., elliptical, spherical, etc.) configuration, as shown in FIG. 1. The struts 1110 extend away from the axis from the proximal end 1106 of the handle 1102 to an intermediate point along the handle 1102. The struts 1110 extend towards the axis from the intermediate point to the distal end 1104 of the handle 1102.

The steerable catheter 1100 comprises an elongate tubular body 1112 positioned distally of the handle 1102. The elongate tubular body 1112 comprises a proximal portion 1114 and a distal portion 1116. A lumen 1118 extends from the proximal portion 1114 to the distal portion 1116. The distal portion 1116 of the tubular body 1112 comprises a resilient component 1120. The resilient component 1120 is positioned at or near the distal end 1122 of the tubular body 1112. The resilient component 1120 may extend proximally from a point at or near the distal end 1122 of the tubular body 1112. In some embodiments, the elongate tubular body 1112 is more malleable towards the distal end 1122 of the tubular body 1112 than towards the proximal end 1114 of the tubular body.

The steerable catheter 1100 comprises a pull wire 1124 extending from the proximal end 1106 of the handle 1102 to the distal end 1122 of the tubular body 1112. The pull wire 1124 is connected to the handle 1102 at or near the proximal end 1106 of the handle and is connected to the elongate tubular body 1112 at or near the distal end 1122 of the body 1112.

The catheter 1100 comprises a first disk 1140 and a second disk 1144 at or near the distal end 1104 of the handle 1102. The first disk 1140 comprises a latch 1142. In some embodiments, the first disk 1140 comprises a greater diameter than the second disk 1144. In some embodiments, the disks 1140, 1144 have the same diameter. In some embodiments, the first disk 1140 comprises a smaller diameter than the second disk 1144. FIG. 11A depicts the first disk 1140 comprising a smaller thickness along the length of the catheter 1000 than the thickness of the second disk 1144. In some embodiments, the first disk 1140 comprises a greater thickness than the second disk 1144. In some embodiments, the first disk 1140 comprises a same thickness as the second disk 1144. The first disk 1140 is depicted as being positioned over or around two parts of the second disk 1144. In some embodiments, the first disk 1140 is proximal or distal to the second disk 1144. In some embodiments, the disks 1140, 1144 are adjacent. In some embodiments, the disks 1140, 1144 may be spaced from one another.

FIG. 11B schematically depicts a cross-sectional view of the second disk 1144 taken along the line B-B. The second disk 1144 may comprise a cross sectional shape similar to the shape of the cross section of the catheter 1000. Other shapes (e.g., square-shaped or elliptical) are also possible. The second disk 1144 comprises a central bore 1150 configured to permit the passage of one or more lumens through the disk 1144. The central bore 1150 is shown as circular, but other shapes are also possible. For example, the central bore 1150 can be ovular or rectangular. The second disk 1144 comprises an eccentric aperture 1148 configured to permit passage of the pull-wire 1124 therethrough. The aperture 1148 is shown as circular, but other shapes (e.g., ovular) are also possible. The second disk 1144 comprises a notch 1146 shaped to mate with the latch 1142 of the first disk 1140. The notch 1146 is shown as rectangular, but other shapes (e.g., triangular, circular) are also possible.

FIG. 11C schematically illustrates a cross-sectional view of the first disk 1140 taken along the line C-C. The first disk 1140 comprises a cross sectional shape similar to the shape of the cross section of the catheter 1000. Other shapes (e.g., square-shaped or elliptical) are also possible. The second disk 1140 comprises a central bore 1152 configured to permit the passage of one or more lumens through the disk 1140. The central bore 1152 is shown as circular, but other shapes are also possible. For example, the central bore 1152 can be ovular or rectangular. The first disk 1140 comprises an eccentric aperture 1154 configured to permit passage of the pull-wire 1124 therethrough. The aperture 1154 is shown as circular, but other shapes (e.g., ovular) are also possible. The first disk 1140 and second disk 1144 are shown as having central bore 1150, 1152 of the same size and shape, but they may be different. The central bores 1150, 1152 may be sized to permit passage of any lumens therethrough. The central bore 1152 may be the size of the central bore 1150 plus the thickness of the second disk 1144. In some embodiments, the apertures 1148, 1154 comprise different shapes and sizes. The apertures 1148, 1154 may have a shape and size selected to permit the passage of a pull wire therethrough. The first disk 1140 comprises a latch 1142 shaped to fit within the notch 1146 of the second disk 1144.

After the distal tip 1116 of the catheter has been deflected, as described above with respect to FIG. 2, the first and second disks 1140, 1144 can be used to lock the distal tip 1116 in a deflected position by holding the pull wire 1122 in a proximally extended position. Prior to deflecting the distal portion 1116 of the catheter 1100, the first disk 1140 can be rotated to a position where the pull wire apertures 1148, 1154 are in alignment. After deflection of the distal tip 1116 of the catheter 1100, the first disk 1140 can be rotated relative to the second disk 1144, creating friction on the pull wire as the pull wire apertures 1148, 1154 move out of alignment. Once sufficient friction is put on the pull wire 1122, the latch 1142 may be locked into the notch 1146, holding the disks 1140, 1144 in an unaligned position and the distal tip 1116 in a deflected position. Locking the catheter 1100 in a deflected position may allow for ease in rotating and steering the catheter, for example because inward pressure on the handle 1102 is not needed to deflect the distal portion 1116.

The first disk 1140 is rotatable relative to the second disk 1144. The second disk 1144 may be fixed in position relative to the catheter 1100, or a portion of the catheter 1000. In some embodiments, both disks 1140, 1144 may be rotatable. Other means for locking the pull wire 1124 in position are also possible For example, the catheter 1100 may comprise a collar positionable around the handle 1102. For another example, the pull wire 1124 may comprise hook-like structures that may engage with other hook like structures of the catheter 1100 (e.g., at the distal end 1104 of the handle 1102).

Although this invention has been disclosed in the context of certain embodiments and examples, it will be understood by those skilled in the art that the invention extends beyond the specifically disclosed embodiments to other alternative embodiments and/or uses of the invention and obvious modifications and equivalents thereof. In addition, while several variations of the embodiments of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the embodiments of the disclosed invention. Thus, it is intended that the scope of the invention herein disclosed should not be limited by the particular embodiments described above.

What is claimed is:

1. A method of using a steerable catheter, the method comprising:

advancing a handle, the handle coupled to an elongate tubular body, the elongate tubular body in a lumen of a patient, the handle comprising a proximal end, a distal end, and an axis between the proximal end of the handle and the distal end of the handle, the handle comprising a plurality of resilient and flexible struts biased into an arcuate configuration, the struts coupled at the proximal end of the handle and the distal end of the handle, the struts extending away from the axis from the proximal end of the handle to an intermediate point along the handle and the struts extending towards the axis from the intermediate point to the distal end of the handle, the struts circumferentially spaced about the axis of the handle forming a generally arcuate shape, and the elongate tubular body comprising a proximal portion and a distal portion, the proximal portion coupled to the distal end of the handle, the distal portion including a distal end of the elongate tubular body, the distal portion comprising a resilient component longitudinally extending along the elongate tubular body proximate to the distal end of the elongate tubular body, a pull wire lumen extending from the proximal portion to the distal portion, a pull wire extending from the proximal end of the handle to the distal end of the elongate tubular body within the pull wire lumen;

manually inwardly compressing the handle, extending the proximal end of the handle and the pull wire proximally and deflecting the distal end of the elongate tubular body from a substantially straight configuration to a curved configuration, a degree of deflecting corresponding to a force applied during the manual inward compression; and rotating the handle including:
continuing manually inwardly compressing the handle; and moving at least one of a thumb forward and fingers backwards, or moving at least one of a thumb backwards and fingers forward.

2. The method of claim 1, wherein the rotating of the handle of the steerable catheter comprises the distal end of the elongate tubular body rotating during or after manually inwardly compressing the handle.

3. The method of claim 1, wherein the rotating of the handle of the steerable catheter comprises rotating the handle between a thumb and fingers of a user of the steerable catheter.

4. The method of claim 1, further comprising manually decompressing the handle, the handle rebounding towards an unbiased configuration, the proximal end of the handle and the pull wire retracting distally, the distal end of the elongate tubular body deflecting from the curved configuration to the substantially straight configuration, a degree of deflection corresponding to a force of manual decompression of the handle.

5. The method of claim 4, further comprising retracting the steerable catheter from the lumen.

6. The method of claim 1, further comprising advancing an endoluminal device through a second lumen of the steerable catheter.

7. The method of claim 1, further comprising locking the pull wire in a proximally extended configuration.

8. The method of claim 1, wherein the resilient component comprises a shape memory material.

9. The method of claim 1, wherein the resilient component is on a side of the elongate tubular member.

10. The method of claim 1, wherein rotating the handle is greater than 360°.

11. A method of using a steerable catheter, the method comprising:
    manually inwardly compressing a handle of the steerable catheter, the handle coupled to an elongate tubular body, the handle comprising a proximal end, a distal end, and an axis between the proximal end of the handle and the distal end of the handle, the handle comprising a plurality of resilient and flexible struts biased into an arcuate configuration, the struts coupled at the proximal end of the handle and the distal end of the handle, the struts extending away from the axis from the proximal end of the handle to an intermediate point along the handle and the struts extending towards the axis from the intermediate point to the distal end of the handle, the struts circumferentially spaced about the axis of the handle, and the elongate tubular body comprising a proximal portion and a distal portion, the proximal portion coupled to the distal end of the handle, the distal portion including a distal end of the elongate tubular body, the distal portion comprising a resilient component longitudinally extending along the elongate tubular body proximate to the distal end of the elongate tubular body, the resilient component on a side of the elongate tubular body, a pull wire extending from the proximal end of the handle to the distal end of the elongate tubular body, wherein manually inwardly compressing the handle comprises extending the proximal end of the handle and the pull wire proximally and deflecting the distal end of the elongate tubular body from a substantially straight configuration to a curved configuration; and
    rotating the handle greater than 360° while continuing manually inwardly compressing the handle.

12. The method of claim 11, wherein the rotating the handle of the steerable catheter comprises the distal end of the elongate tubular body rotating during or after manually inwardly compressing the handle, and wherein the rotating of the handle of the steerable catheter comprises rotating the handle between a thumb and fingers of a user of the steerable catheter.

13. The method of claim 11, further comprising advancing an endoluminal device through a lumen of the steerable catheter.

14. The method of claim 11, wherein a degree of deflecting corresponds to a force applied during the manual inward compression.

15. The method of claim 11, further comprising locking the pull wire in a proximally extended configuration.

16. The method of claim 11, further comprising manually decompressing the handle, the handle rebounding towards an unbiased configuration, the proximal end of the handle and the pull wire retracting distally, the distal end of the elongate tubular body deflecting from the curved configuration to the substantially straight configuration, a degree of deflection corresponding to a force of manual decompression of the handle.

* * * * *

UNITED STATES PATENT AND TRADEMARK OFFICE
CERTIFICATE OF CORRECTION

Page 1 of 1

PATENT NO. : 9,636,480 B2
APPLICATION NO. : 13/801888
DATED : May 2, 2017
INVENTOR(S) : Matthew W. Sevensma It is certified that error appears in the above-identified patent and that said Letters Patent is hereby corrected as shown below:

At Column 16, Line 22 (approximately), in Claim 12, after "rotating" insert --of--.

Signed and Sealed this
Thirty-first Day of October, 2017

Joseph Matal
*Performing the Functions and Duties of the*
*Under Secretary of Commerce for Intellectual Property and*
*Director of the United States Patent and Trademark Office*